(12) United States Patent
Takahashi et al.

(10) Patent No.: US 7,442,942 B2
(45) Date of Patent: Oct. 28, 2008

(54) CHARGED PARTICLE BEAM APPARATUS

(75) Inventors: Haruo Takahashi, Chiba (JP); Toshiaki Fujii, Chiba (JP); Yutaka Ikku, Chiba (JP); Kouji Iwasaki, Chiba (JP); Yo Yamamoto, Chiba (JP)

(73) Assignee: SII Nanotechnology Inc. (JP)

( * ) Notice: Subject to any disclaimer, the term of this patent is extended or adjusted under 35 U.S.C. 154(b) by 229 days.

(21) Appl. No.: 11/509,520

(22) Filed: Aug. 24, 2006

(65) Prior Publication Data

US 2007/0045560 A1 Mar. 1, 2007

(30) Foreign Application Priority Data

Aug. 31, 2005 (JP) ............................. 2005-251415

(51) Int. Cl.
*H01J 37/20* (2006.01)
(52) U.S. Cl. ............................ 250/442.11; 250/492.21; 250/309; 250/310
(58) Field of Classification Search ............ 250/442.11, 250/492.21, 309, 310
See application file for complete search history.

(56) References Cited

U.S. PATENT DOCUMENTS 7,268,356 B2 * 9/2007 Shichi et al. ............ 250/492.21
7,381,968 B2 * 6/2008 Tanaka et al. ............ 250/440.11

* cited by examiner

*Primary Examiner*—Kiet T Nguyen
(74) *Attorney, Agent, or Firm*—Adams & Wilks

(57) ABSTRACT

To include a focused ion beam apparatus fabricating a sliced specimen by processing a specimen as well as observing the sliced specimen, a scanning electron microscope observing the slice specimen, a gas.-ion beam irradiation apparatus performing finishing processing by irradiating a gas-ion beam onto a surface of the sliced specimen, a specimen stage on which the sliced specimen is fixed and having at least one or more rotation axis, a specimen posture recognition means recognizing positional relation of the sliced specimen with respect to the specimen stage and a specimen stage control means controlling the specimen stage based on a specimen posture recognized by the posture recognition means and an installation angle of the gas-ion beam irradiation apparatus in order to allow an incident angle of the gas-ion beam with respect to the obverse or the reverse of the sliced specimen to be a desired value.

5 Claims, 2 Drawing Sheets

FIG. 2
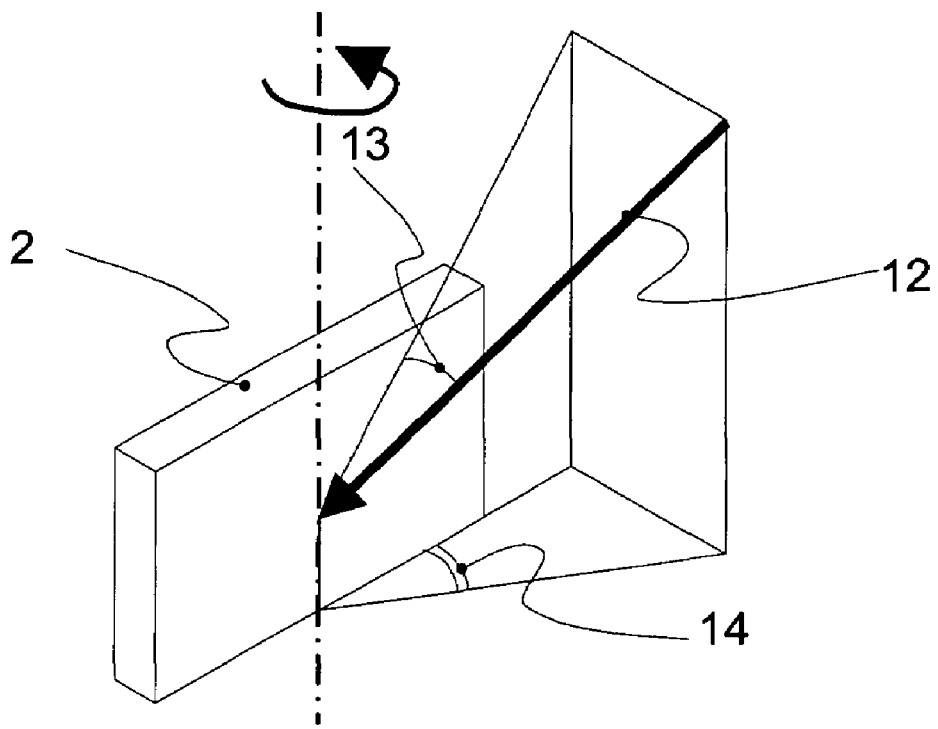
FIG. 3A  FIG. 3B  FIG. 3C
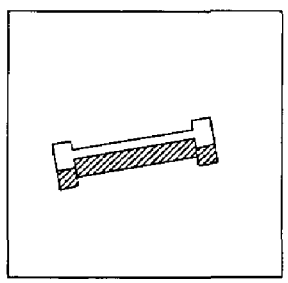 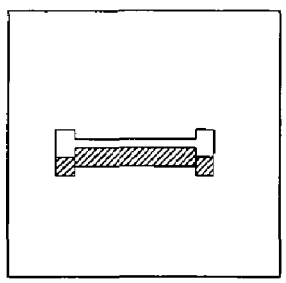 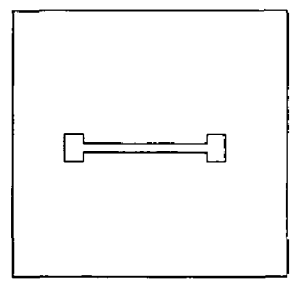

CHARGED PARTICLE BEAM APPARATUS

BACKGROUND OF THE INVENTION

The invention relates to a charged particle beam apparatus for making a sliced specimen to be observed by a transmission electron microscope (TEM).

In recent years, as miniaturization of a pattern of a semiconductor device proceeds, importance of technology of observing and evaluating a particular minute portion of the semiconductor device using a Transmission Electron Microscope (TEM) increases. In order to fabricate a sliced specimen to be such particular minute portion, a focused ion beam apparatus is widely used, however, there arises a problem of damage by a focused ion beam as the required thickness of the specimen becomes thinner, and a method for preventing damage is needed.

As the solution for the above state, for example, a method of irradiating a gas-ion beam using an element whose chemical activity is low such as argon as ionic species is proposed (refer to Patent document 1). Since an argon ion milling apparatus which is widely used at present is a dedicated device having a single function, positional relation between the specimen and the ion beam is a simple, an irradiation angle of the ion beam can be easily set by setting a tilt of a specimen stage, and arrangement is instinctively comprehensible. However, when the actual sliced specimen is inclined or bending with respect to the stage, the specimen cannot be recognized, therefore, there was a problem that it was difficult to precisely control the irradiation angle. An incident angle is an important parameter which affects an etching rate and the like, therefore, accurate incident angle control has been required.

On the other hand, an apparatus incorporating a mechanism of irradiating a gas-ion beam such as argon with the focused ion beam apparatus is also proposed (for example, refer to Patent document 2). In such composite apparatus, the irradiation angle of the argon-ion beam is fixed in a parallel movement or in a rotation direction with respect to an axis of the focused ion beam or a scanning electron microscope, for convenience of processing, observation and so on. Accordingly, an installation angle of the mechanism of irradiating the argon-ion beam has to be an angle not parallel, or not orthogonal to the rotation axis of the stage. In this case, as an example is shown in FIG. 2, a rotation angle 14 of the specimen stage is not equal to an incident angle 13 of the beam 12 to a specimen surface. Therefore, it is difficult to instinctively comprehend the incident angle of the argon-ion beam with respect to the surface of the specimen 2. It is necessary to perform stage operation by calculating a required movement amount of the stage for the irradiation at the desired angle. It is required to solve the problem from viewpoints of operational efficiency and of occurring man-caused mistakes.

[Patent document 1] JP-A-10-221227
[Patent document 2] JP-A-6-2601129

In view of the above, an object of the invention is to provide a charged particle beam apparatus capable of controlling an irradiation angle of a gas-ion beam accurately and easily according to an arrangement state of a sliced specimen.

SUMMARY OF THE INVENTION

In a first aspect of the invention for solving the problems, when a finishing processing of a sliced specimen is performed by a charged particle beam apparatus including a focused ion beam apparatus fabricating the sliced specimen by processing a specimen as well as observing the sliced specimen, a scanning electron microscope observing the sliced specimen, a gas-ion beam irradiation apparatus performing finishing processing by irradiating a gas-ion beam onto a surface of the sliced specimen, and a specimen stage on which the sliced specimen is fixed and having at least one or more rotation axis, positional relation of the sliced specimen with respect to the specimen stage is recognized by using a specimen posture recognition means. In order to allow an incident angle of the gas-ion beam with respect to the surface of the sliced specimen to be a desired value, a specimen stage control means is used, in which what amount the specimen stage should be moved from a present position is calculated based on the specimen posture recognized by the posture recognition means and an installation angle of the gas-ion beam irradiation apparatus, and the specimen stage is moved according to the calculated result. As a result, the gas-ion beam can be irradiated on the surface of the sliced specimen at the desired incident angle accurately and easily. In this aspect, a configuration in which only either the focused ion beam apparatus or the scanning electron microscope is included can obtain the same advantage. It is also possible to obtain the same advantage by using the same method with respect to not only the obverse of the sliced specimen but also the reverse.

In a second aspect of the invention, as the specimen posture recognition means in the first aspect, positional relation of the sliced specimen with respect to the specimen stage is recognized based on an observation image of the sliced specimen by the focused ion beam apparatus and coordinates of the specimen stage at the time of observation, thereby irradiating the gas-ion beam onto the surface of the sliced specimen at the desired incident angle accurately and easily. It is also possible to obtain the same advantage by using an observation image by the scanning electron microscope, instead of using the observation image of the sliced specimen by the focused ion beam apparatus in this aspect.

In a third aspect of the invention, in the first aspect or the second aspect, any one or plural gas-ion beams of neon, argon, krypton, xenon or nitrogen are applied as the gas-ion beam. According to this, the gas-ion beam can be irradiated onto the surface of the sliced specimen at the desired incident angle accurately and easily.

In a fourth aspect of the invention, in any of the first to third aspects, the specimen stage is configured to be a five-axis stage having a tilt axis which is orthogonal to axes of the focused ion beam apparatus and the scanning electron microscope, a three-axis orthogonal stage which rotates with the rotation of the tilt axis and a rotation axis which is placed on the three-axis orthogonal stage. The five axes in the five-axis stage are the tilt axis, the rotation axis, the X axis, the Y axis, and the Z axis. According to this, the gas-ion beam can be irradiated onto the surface of the sliced specimen at the desired angle accurately and easily.

In a fifth aspect of the invention, in the fourth aspect, the axis of the focused ion beam apparatus, the axis of the scanning electron microscope and a axis of the gas-ion beam irradiation apparatus substantially intersect at one point, further, the axis of the gas-ion beam irradiation apparatus is configured to be on a plane including the tilt axis and the axis of either the focused ion beam apparatus or the scanning electron microscope, as well as to have an angle which is orthogonal or not parallel to the tilt axis. According to this, the gas-ion beam can be irradiated to the surface of the sliced specimen at the desired angle accurately and easily.

[Advantage of the Invention]

According to the invention, as described above, it becomes possible to provide a charged particle beam apparatus capable of controlling an irradiation angle of a gas-ion beam accurately and easily according to the arrangement state of the sliced specimen.

BRIEF DESCRIPTION OF THE DRAWINGS

FIG. 2 is a view explaining an example of a specimen posture recognition means according to the embodiment 1 of the invention.

FIG. 3A to FIG. 3C are views showing the relation between rotation angles of a stage and incident angles to a specimen.

Figure 1:
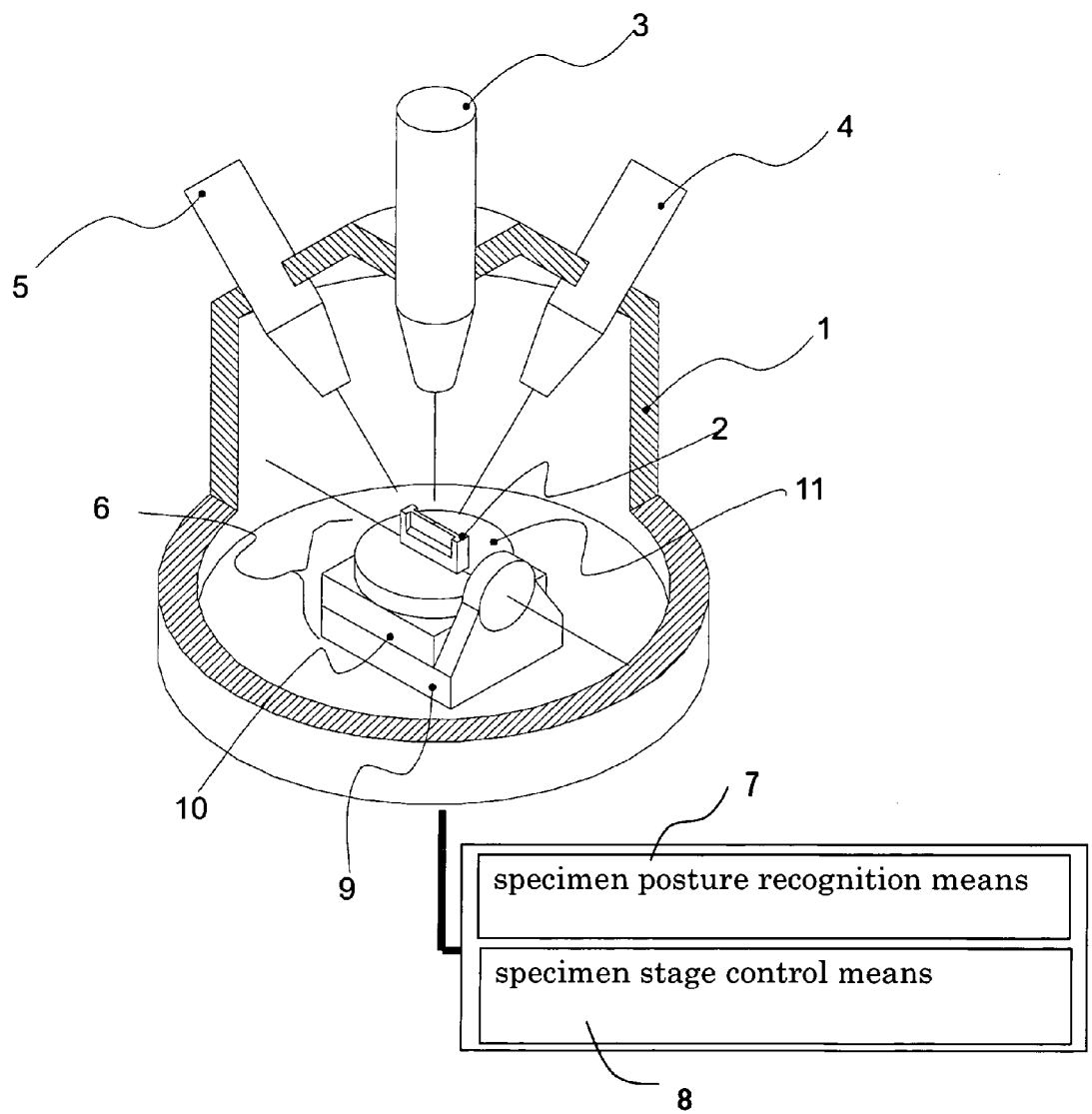
FIG. 1 is a view showing a schematic configuration of a charged particle beam apparatus according to an embodiment 1 of the invention.

DESCRIPTION OF REFERENCE NUMERALS 1 specimen chamber
2 sliced specimen
3 focused ion beam apparatus
4 scanning electron microscope
5 gas-ion beam irradiation apparatus
6 specimen stage
7 specimen posture recognition means
8 specimen stage control means
9 tilt stage
10 XYZ stage
11 rotation stage
12 gas-ion beam
13 gas-ion beam irradiation angle
14 stage rotation angle

DETAILED DESCRIPTION OF THE INVENTION

Hereinafter, the best mode for carrying out the invention will be explained with reference to the drawings. The description for embodiments is exemplification and the structure of the invention is not limited to the following description.

Embodiment 1

FIG. 1 is a schematic view showing an outline of a charged particle beam apparatus according to an embodiment 1 of the invention. In the embodiment, the explanation will be made on the assumption that a specimen is fixed on a stage as the specimen (hereinafter, referred to as a sliced specimen) which has been sliced to some degree using a focused ion beam apparatus and the like. Though omitted in FIG. 1, the sliced specimen is fixed on a specimen stage called as a "mesh" which is used when observed by TEM and fixed on a specimen stage 6 through the mesh. The meaning of "to be sliced to some degree" differs greatly depending on a specimen, an observation object thereof or the like, however, the thickness of the specimen is not related to the essence of the invention. To cite one example, the specimen which is sliced to the thickness of approximately 100 to 200 nanometers is used.

As shown in FIG. 1, the charged particle beam apparatus according to the embodiment includes, in a specimen chamber 1 the interior of which is maintained in a vacuum state by a not-shown vacuum evacuation pump, a focused ion beam apparatus 3 fabricating a sliced specimen 2 by processing a surface of the specimen as well as observing the sliced specimen 2, a scanning electron microscope 4 observing the sliced specimen 2, a gas-ion beam irradiation apparatus 5 performing finishing processing by irradiating a gas ion beam 12 onto the sliced specimen 2, and a specimen stage 6 on which the sliced specimen is fixed and having at least one or more rotation axis. For the gas-ion beam irradiation apparatus 5, an argon-ion beam irradiation apparatus is used, in which argon gas is ionized and irradiated at low acceleration voltage of approximately 1 kV. The focused ion beam apparatus 3 is disposed vertically, the scanning electron microscope 4 and the gas-ion beam irradiation apparatus 5 are disposed obliquely, and axes of these three beams are disposed so as to substantially intersect at one point. Further, the specimen stage 6 is a five-axis eucentric stage which has a tilt stage 9 rotating along an axis including an intersection of lens barrel axes of the focused ion beam apparatus 3 and the scanning electron microscope 4 as well as orthogonal to respective axes thereof, an XYZ stage 10 of orthogonal three axes, which is placed on the tilt stage, and a rotation stage 11 placed on the XYZ stage 10 and rotating about the center axis of a vertical direction (Z direction).

A relative positional relation of the sliced specimen 2 fixed on the specimen stage 6 with respect to the specimen stage 6 can be captured by a specimen posture recognition means 7. The posture recognition of the sliced specimen 2 by the specimen posture recognition means 7 is realized, for example, using a method explained as follows. First, the sliced specimen 2 is mounted on a eucentric position. For that operation, a method of searching a position where an image does not move when moving a tilt axis of the tilt stage 9 is widely used. Secondly, an observation image of the sliced specimen 2 is obtained by the focused ion beam apparatus 3. The observation image is, for example, one which is shown in FIG. 3A. At this time, in order to avoid damage of the specimen by etching, it is necessary to be sufficiently careful in an electric current value or scanning time of the beam for observation. In the observation image, the rotation stage 11 is rotated about the center axis of the Z direction so that an upper edge of the sliced specimen 2 corresponds to the direction of the tilt axis of the tilt stage 9 as shown in FIG. 3B. The operation is performed easily by making an adjustment in advance so that the direction of the tilt axis of the tilt stage 9 corresponds to an angle which is comprehensible such as a horizontal angle or a vertical angle on a screen. In the case that the sliced specimen 2 is not on the rotation center of the rotation stage 11, it is also necessary to operate the XYZ stage 10 when rotated, however, explanation in detail thereof is omitted because it is widely performed in general. Thirdly, the tilt stage 9 is operated so that the sliced specimen 2 can be seen from just above. Specifically, the adjustment is made so that only the upper edge of the sliced specimen 2 can be seen and wall surfaces thereof are hardly seen, as shown in FIG. 3C. For convenience of subsequent explanation, a side facing the scanning electron microscope 4 at this time is defined as a surface. Fourthly, a tilt angle and a rotation angle of the specimen stage 6 at this time are recorded. The angle is the angle of the sliced specimen 2 with respect to the specimen stage 6, and it is considered that the posture can be recognized. The specimen posture recognition means was performed based on the observation image of the focused ion beam apparatus 3 in this case, however, since the positional relation between the scanning electron microscope 4 and the focused ion beam apparatus 3 is a constant which is decided by respective installation angles, the posture of the sliced specimen 2 with respect to the specimen stage 6 can be recognized in the same way when the same operation is performed based on an observation image of the scanning electron microscope 4. The focused ion beam apparatus 3 is usually used at an acceleration voltage of approximately 30 kV in many cases, therefore, observation by the scanning electron microscope 4 causes little damage to the sliced specimen 2 in many cases. Accordingly, in the case of an additional process of a finishing process, there is a case when the observation image of the scanning electron microscope 4 is used.

As described above, the posture of the sliced specimen 2 can be recognized by the posture recognition means 7. A stage movement amount for obtaining a desired incident angle is calculated based on the information. When there is a stage having a rotation axis which is orthogonal to the lens barrel axis of the gas-ion beam irradiation apparatus 5, the angle calculation is easy enough to be performed instinctively, however, when there is not the rotation axis which is orthogonal to the gas-ion beam irradiation apparatus 5 as in the illustrated embodiment, the following calculation will be performed.

A normal vector on a surface of the sliced specimen 2 which is expressed in a coordinate system fixed on a surface of the specimen stage 6 is represented as "ns". Components of the normal vector "ns" can be obtained by the above specimen posture recognition means. The vector "ns" can be transformed into a normal vector "nt" of the sliced specimen 2 expressed in the coordinate system, which is fixed on the tilt stage, by a matrix "R" expressing a rotation of the rotation stage. Further, it can be transformed into a normal vector "nc" of the sliced specimen 2 expressed in the coordinate system, which is fixed in the specimen chamber 1, by a matrix "T" expressing a rotation of the tilt stage in the same way (mathematical expression 1).

$$nc = T \cdot R \cdot ns \qquad \text{Mathematical expression 1}$$

On the other hand, a vector expressing a traveling direction of a gas-ion beam irradiated from the gas-ion beam irradiation apparatus 5 can be expressed immediately in the coordinate system fixed in the specimen chamber 1 from the installation angle thereof. When the vector expressing the traveling direction of the gas-ion beam is represented as "bc", an incident angle α to the sliced specimen 2 is calculated by subtracting an angle between the normal vector of the sliced specimen 2 and the vector of gas-ion beam traveling direction from 90°, therefore, the angle is expressed by the definition of a vector scalar product as below:

$$\cos\alpha = \frac{\vec{nc} \cdot \vec{bc}}{|\vec{nc}||\vec{bc}|} \qquad \text{Mathematical expression 2}$$

The vector "nc" includes a rotation angle "t" of the tilt stage 9, a rotation angle "r" of the rotation stage 11 and a tilt "τ", a rotation angle "ρ" of the sliced specimen 2 with respect to the specimen stage 6. The vector "bc" is a constant which is decided by the installation angle of the gas-ion beam irradiation apparatus 5, therefore, it is considered that the right side of the mathematical expression 2 is a function of the rotation angle "t" of the tilt stage 9, the rotation angle "r" of the rotation stage and the tilt "τ", the rotation angle "ρ" of the sliced specimen 2 with respect to the specimen stage 6. The movement amount of the specimen stage 6 with respect the desired incident angle can be calculated assigning the value obtained by the above specimen posture recognition means 7 to "τ", "ρ" and solving for "r" in the state that "t" is fixed. In this case, sometimes there are two solutions, however, the solution can be selected by attaching a condition of minimizing the movement amount of the specimen stage 6 or a condition that the processed surface can be observed by the scanning electron microscope 4. Concerning a rear surface, a required movement amount of the specimen stage 6 can be calculated by making a sign of the incident angle α negative to solve the expression. The specimen stage 6 is moved based on the calculated result. The above is the explanation of a specimen stage control means 8. In the example, the expression is solved for "r" in the state that "t" is fixed, which represents that the irradiation angle is decided only by the rotation of the rotation stage 11, however, it may be solved for "t" in the state that "r" is fixed, which does not limit the invention at all.

The above is the explanation for the control of the gas-ion beam irradiation angle by the charged particle beam apparatus according to the invention.

Looking back on the explanation until now from an operational viewpoint by an operator, first, the specimen stage is operated so that the sliced specimen 2 can be seen from just above. Next, the incident angle and that the gas-ion beam is irradiated to either the obverse or reverse surface are designated. When designating the incident angle, it is not necessary that the operator is conscious of the installation angle of the gas-ion beam irradiation apparatus 5 and the like, therefore, operation can be performed extremely easily.

As described above, according to the invention, it is possible to provide the charged particle beam apparatus capable of controlling the irradiation angle of the gas-ion beam accurately and easily according to the arrangement state of the sliced specimen.

Another embodiment

In the above embodiment 1, both the focused ion beam apparatus 3 and the scanning electron microscope 4 are mounted, however, the specimen posture recognition means can be executed in the same way by combining either one of them with the gas-ion beam irradiation apparatus. As a result, it is possible to provide a charged particle beam apparatus capable of controlling the irradiation angle of the gas-ion beam accurately and easily according to the arrangement state of the sliced specimen.

The specimen posture recognition means can be operated by the operator so that the sliced specimen 2 is seen in a designated way, however, it is possible to execute the means automatically by using image recognition technology, which is included in disclosure of the invention.

When it is not necessary to involve the stage operation in the process of the specimen posture recognition, in the case that either the tilt stage 9 or the rotation stage 11 is not mounted in the explanation of the embodiment 1, the invention can be realized.

What is claimed is:

1. A charged particle beam apparatus comprising:
   a focused ion beam apparatus fabricating a sliced specimen by processing a specimen as well as observing the sliced specimen;
   a scanning electron microscope observing the sliced specimen;
   a gas-ion beam irradiation apparatus performing finishing processing by irradiating a gas-ion beam onto a surface of the sliced specimen;
   a specimen stage on which the sliced specimen is fixed and having at least one rotation axis;
   a specimen posture recognition means recognizing positional relation of the sliced specimen with respect to the specimen stage; and
   a specimen stage control means controlling the specimen stage based on a specimen posture recognized by the posture recognition means and an installation angle of a lens barrel of the gas-ion beam irradiation apparatus in order to allow an incident angle of the gas-ion beam with respect to the obverse or the reverse of the sliced specimen to be a desired value.

2. The charged particle beam apparatus according to claim 1, wherein the specimen posture recognition means recognizes positional relation of the sliced specimen with respect to the specimen stage based on an observation image of the sliced specimen by the focused ion beam apparatus or the scanning electron microscope, and coordinates of the specimen stage at the time of observation.

3. The charged particle beam apparatus according to claim 1, wherein any one of plural gas-ion beams of neon, argon, krypton, xenon and nitrogen is applied as the gas-ion beam.

4. The charged particle beam apparatus according to claim 1, wherein the specimen stage is a five-axis stage having a tilt axis which is orthogonal to lens barrel axes of the focused ion beam apparatus and the scanning electron microscope, a three-axis orthogonal stage which rotates with the rotation of the tilt axis and a rotation axis which is placed on the three-axis orthogonal stage.

5. The charged particle beam apparatus according to claim 4, wherein axes of the focused ion beam apparatus and the scanning electron microscope and a axis of the gas-ion beam irradiation apparatus substantially intersect at one point, further, the axis of the gas-ion beam irradiation apparatus is on a plane including the tilt axis and the axis of either the focused ion beam apparatus or the scanning electron microscope, as well as has an angle which is orthogonal or not parallel to the tilt axis.

* * * * *